United States Patent
McDonnell et al.

(10) Patent No.: US 6,936,434 B2
(45) Date of Patent: Aug. 30, 2005

(54) VAPOR PHASE DECONTAMINATION PROCESS BIOLOGICAL INDICATOR EVALUATOR RESISTOMER (BIER) VESSEL

(75) Inventors: Gerald E. McDonnell, Chardon, OH (US); Iain F. McVey, Lakewood, OH (US); Michael Geanous, Erie, PA (US)

(73) Assignee: Steris Inc., Temecula, CA (US)

( * ) Notice: Subject to any disclaimer, the term of this patent is extended or adjusted under 35 U.S.C. 154(b) by 0 days.

(21) Appl. No.: 10/124,384

(22) Filed: Apr. 17, 2002

(65) Prior Publication Data

US 2002/0160440 A1 Oct. 31, 2002

Related U.S. Application Data

(60) Provisional application No. 60/284,426, filed on Apr. 17, 2001.

(51) Int. Cl.[7] ............................. C12Q 1/22; C12Q 1/02; C12Q 1/00; C12M 1/34; A61L 2/08
(52) U.S. Cl. ................................. 435/31; 435/29; 435/4; 435/287.5; 435/807; 422/26; 422/27; 422/28
(58) Field of Search ................................. 435/31, 29, 4, 435/287.5, 807, 28; 422/26, 27

(56) References Cited

U.S. PATENT DOCUMENTS

| | | | |
|---|---|---|---|
| 4,158,040 A | 6/1979 | Miraldi | 422/297 |
| 4,169,123 A | 9/1979 | Moore et al. | 422/29 |
| 4,744,951 A | 5/1988 | Cummings et al. | 422/28 |
| 4,909,999 A | 3/1990 | Cummings et al. | 422/298 |
| 4,952,370 A | 8/1990 | Cummings et al. | 422/28 |
| 4,956,145 A | 9/1990 | Cummings et al. | 422/28 |
| 5,152,968 A | * 10/1992 | Foti et al. | 422/304 |
| 5,445,792 A | 8/1995 | Rickloff et al. | 422/28 |
| 5,482,684 A | 1/1996 | Martens et al. | 422/119 |
| 5,498,526 A | 3/1996 | Caputo et al. | 435/31 |
| 5,759,848 A | 6/1998 | Nagoshi et al. | 435/287.1 |
| 5,788,925 A | 8/1998 | Pai et al. | 422/3 |
| 5,801,010 A | 9/1998 | Falkowski et al. | 435/31 |
| 5,834,313 A | * 11/1998 | Lin | 436/1 |
| 5,869,000 A | * 2/1999 | DeCato | 422/33 |
| 5,872,359 A | 2/1999 | Stewart et al. | 250/339.13 |
| 5,876,664 A | 3/1999 | Childers et al. | 422/28 |
| 5,906,794 A | 5/1999 | Childers | 422/28 |
| 6,036,918 A | * 3/2000 | Kowanko | 422/33 |
| 6,077,480 A | * 6/2000 | Edwards et al. | 422/28 |
| 2002/0160440 A1 | * 10/2002 | McDonnell et al. | 435/31 |
| 2003/0086820 A1 | * 5/2003 | McDonnell et al. | 422/28 |

* cited by examiner

Primary Examiner—Louise N. Leary
(74) Attorney, Agent, or Firm—Fay, Sharpe, Fagan, Minnich & McKee, LLP

(57) ABSTRACT

A BIER vessel evaluates biological indicators for sterilization processes. By flowing gaseous sterilant, such as vaporized hydrogen peroxide, through a chamber (12) before, during, and after introducing the indicators, the indicators are instantaneously exposed to preselected steady state conditions, allowing accurate and reproducible evaluation of the indicator response. A door (32) to an opening (30) in the chamber opens for introducing the indicators to the chamber without appreciably disturbing the steady state conditions therein. After a preselected time, the biological indicators are removed and evaluated for remaining biological activity.

28 Claims, 4 Drawing Sheets

VAPOR PHASE DECONTAMINATION PROCESS BIOLOGICAL INDICATOR EVALUATOR RESISTOMER (BIER) VESSEL

This application claims the priority of U.S. Provisional Application Ser. No. 60/284,426, filed Apr. 17, 2001.

BACKGROUND OF THE INVENTION

The present invention relates to the sterilization arts. It finds particular application in conjunction with biological indicator evaluator resistomer (BIER) vessels for evaluating biological indicators used for determining the effectiveness of vaporized hydrogen peroxide (VHP) sterilization processes and will be described with particular reference thereto. It should be appreciated, however, that the invention is also applicable to use with other sterilants, including ethylene oxide, steam, other oxidants in the vapor phase, such as peracetic acid, and the like.

Sterilization and disinfection are important tools for destroying harmful organisms which may otherwise contaminate medical, dental, surgical, pharmaceutical, food processing, and other equipment. Vaporized hydrogen peroxide is a particularly useful agent for this purpose. Because it is effective at low temperatures (below 80° C.), thermal degradation of materials susceptible to heat, such as medical and dental instruments, plastic, containers, and plastic contact lenses, is avoided. In addition, decomposition of the vapor results in the formation of water and oxygen, which are environmentally and biologically safe by-products.

BIER vessels are widely used for the purpose of evaluating the performance characteristics of biological indicators of the type used in the medical industry for ensuring adequate sterilization of equipment. Biological indicators typically employ a calibrated population of microbial spores which are subjected to the decontamination process. Remaining spore viability following the process is indicative of a processing defect.

BIER vessels differ from conventional sterilizers in that they allow a high level of control and monitoring of the process conditions within the vessel. Such vessels commonly employ a small (about 10–30 liters), temperature-controlled chamber. Ideally, during evaluation of a biological indicator, the indicator is exposed within the BIER vessel under equilibrium conditions with respect to the sterilant in terms of pressure, temperature, relative humidity and sterilant concentration for a selected time period. BIER vessels are designed to both generate and end the equilibrium (or square wave) conditions "instantaneously," by rapid introduction of the sterilant to the vessel at the required temperature and pressure and subsequent evacuation on completion of the exposure to the sterilant. Instantaneous exposure to, and subsequent evacuation or flushing of the sterilant from the chamber eliminates residual kill of the test microorganisms and provides an accurate assessment of the biological indicator relative to the particular agent being evaluated.

Current BIER vessel technology is adapted specifically for one of two agents: steam or ethylene oxide gas. For both of these agents, steady state conditions are readily achieved, virtually instantaneously. In the case of steam, steady state conditions are achieved in minimal time, for a relatively small chamber, by rapid introduction of the steam under pressure into the chamber. The environment is sustained by intermittent pulsing of steam into the chamber as necessary to maintain a selected temperature and pressure. In the case of ethylene oxide, uniform chamber conditions are achieved by a single injection of a specified volume of gas. As with a steam BIER vessel, the introduction of the agent to a small chamber and the time in which steady state conditions are achieved can be considered instantaneous for ethylene oxide.

The technology developed for use with steam and ethylene oxide agents is unsuited to use with vaporized hydrogen peroxide. Vaporized hydrogen peroxide is a unique sterilant, requiring low vapor pressure for effective sterilization. High pressures cause condensation of the gas, reducing its effectiveness as a sterilant and disinfectant. High temperatures tend to cause decomposition of the gas at both atmospheric and vacuum pressures. In addition, hydrogen peroxide gas is highly reactive, decomposing upon contact with a wide variety of inorganic and organic substances. A single injection of hydrogen peroxide, or intermittent pulses, are generally ineffective as the gas does not remain intact for prolonged periods due to its reactivity. The rate of degradation is difficult to predict since it varies due to a number of factors, including temperature, absorbency of the load, and the like. Conventional methods of achieving equilibrium conditions are therefore unsuited for use with vaporized hydrogen peroxide.

Further, conventional systems for evaluating biological indicators employ a flexible walled chamber, or isolator, which does not allow for optimal temperature control, thorough mixing of the agent throughout the chamber, or sub-atmospheric pressure control.

The release of the sterilant into a closed chamber affects the pressure within the chamber. The effect is most pronounced when the system is operating under a high vacuum. Under such conditions, small fluctuations in the weight of sterilant released have a relatively large influence on the chamber pressure. Where diluting gases are present in the chamber, changes in pressure tend to affect the antimicrobial activity of the sterilant by altering the mean free path of the gas molecules, resulting in changes in the frequency with which the sterilant molecules come into contact with the surfaces of the material being exposed to the sterilant.

The present invention provides a new and improved BIER vessel and method of operation which overcome the above referenced problems, with respect to vaporized hydrogen peroxide, and others.

SUMMARY OF THE INVENTION

In accordance with one aspect of the present invention, a system for evaluating biological indicators is provided. The system includes a chamber and an access port for selectively introducing biological indicators into the chamber and for subsequently removing the biological indicators from the chamber. A generator is provided for generating a multi-component sterilant vapor. A circulating system supplies the multi-component sterilant vapor to the chamber. A source of a first component of the multi-component sterilant vapor is fluidly connected with the vaporizer. A source of a second component of the multi-component sterilant vapor is fluidly connected with the vaporizer.

In accordance with another aspect of the present invention, a system for evaluating biological indicators is provided. The system includes a chamber. An access port is provided for selectively introducing biological indicators into the chamber and for subsequently removing the biological indicators from the chamber. The access port includes a tube having a cross section shaped to receive a sample holder therethrough and an opening in fluid communication with the chamber at one end thereof. A valve selectively closes the opening. A generator generates a multi-component sterilant vapor. A circulating system supplies the multi-component sterilant vapor to the chamber.

In accordance with another aspect of the present invention, a method of evaluating a biological indicator is provided. The method includes generating a multi-component vapor from a first component and a second component. The multi-component vapor is passed through a test chamber until steady state conditions are achieved. The biological indicator to be evaluated is introduced into the chamber. The steady state conditions are maintained for a selected period, including adjusting a ratio of the first component to the second component in the multi-component vapor and introducing the adjusted multi-component vapor to the test chamber. The biological indicator is removed from the test chamber after a preselected time period and the effects upon the indicator are assessed.

In accordance with another aspect of the present invention, an evaluation system is provided. The system includes a vessel which defines an interior chamber. A source of an antimicrobial fluid supplies the antimicrobial fluid to the chamber. A tube is fluidly connected with the chamber. The tube extends from the vessel for receiving a sample holder therein. The sample holder carries a sample to be evaluated and is movable within the tube between a first position, in which the sample is positioned outside the chamber and a second position, in which the sample is positioned inside the chamber to be exposed to the antimicrobial fluid. A means for applying suction to the chamber is provided. A means is associated with at least one of the tube and the sample holder for resisting movement of the sample holder into the chamber under the influence of a reduced pressure applied by the suction means.

In accordance with another aspect of the present invention, a method of evaluating an effect of an antimicrobial process upon an indicator for the process is provided. The method includes supplying an antimicrobial fluid to the chamber, positioning the indicator on a sample holder, inserting the sample holder into a first end of a tube which is fluidly connected with a chamber at a second end, and opening a valve which seals the chamber from the second end of the tube. The method further includes pushing the sample holder through the tube until the indicator is positioned within the chamber and exposing the indicator to the antimicrobial fluid in the chamber. The sample holder is withdrawn from the chamber and the indicator evaluated to determine the effect of the antimicrobial process upon the indicator.

One advantage of the present invention is that a reproducible vaporized hydrogen peroxide environment is created for evaluation of biological indicators.

Another advantage of the present invention is that a homogeneous distribution of the sterilant within the chamber is achieved.

Another advantage of the present invention is that the agent is flowed through the chamber, thereby exposing the biological indicator to a continuous stream of fresh sterilant.

Still further advantages of the present invention will become apparent to those of ordinary skill in the art upon reading and understanding the following detailed description of the preferred embodiments.

BRIEF DESCRIPTION OF THE DRAWINGS

The invention may take form in various components and arrangements of components, and in various steps and arrangements of steps. The drawings are only for purposes of illustrating a preferred embodiment and are not to be construed as limiting the invention.

DETAILED DESCRIPTION OF THE PREFERRED EMBODIMENTS

Figure 1:
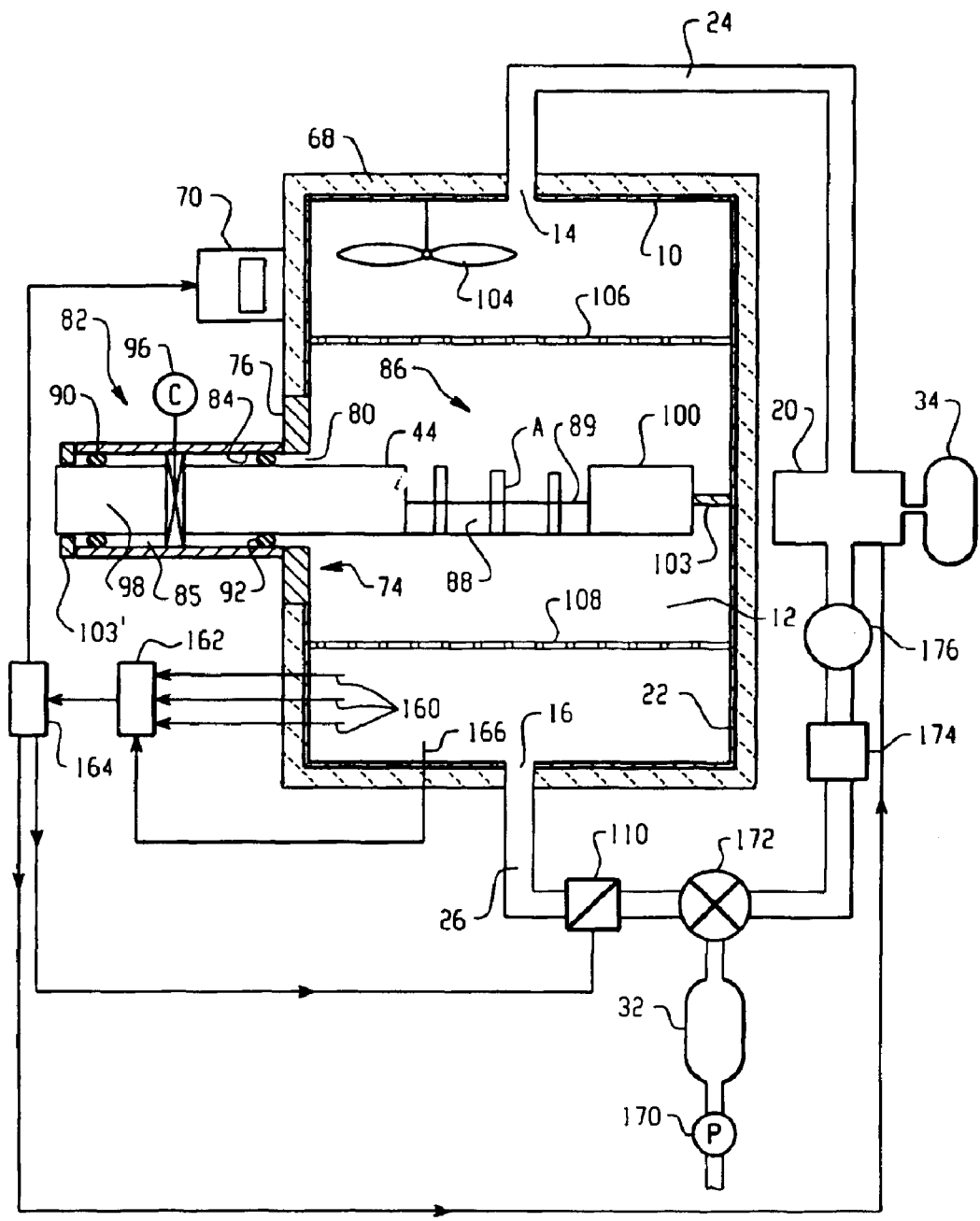
FIG. 1 is a cross section of a BIER vessel in accordance with the present invention.
Figure 2:
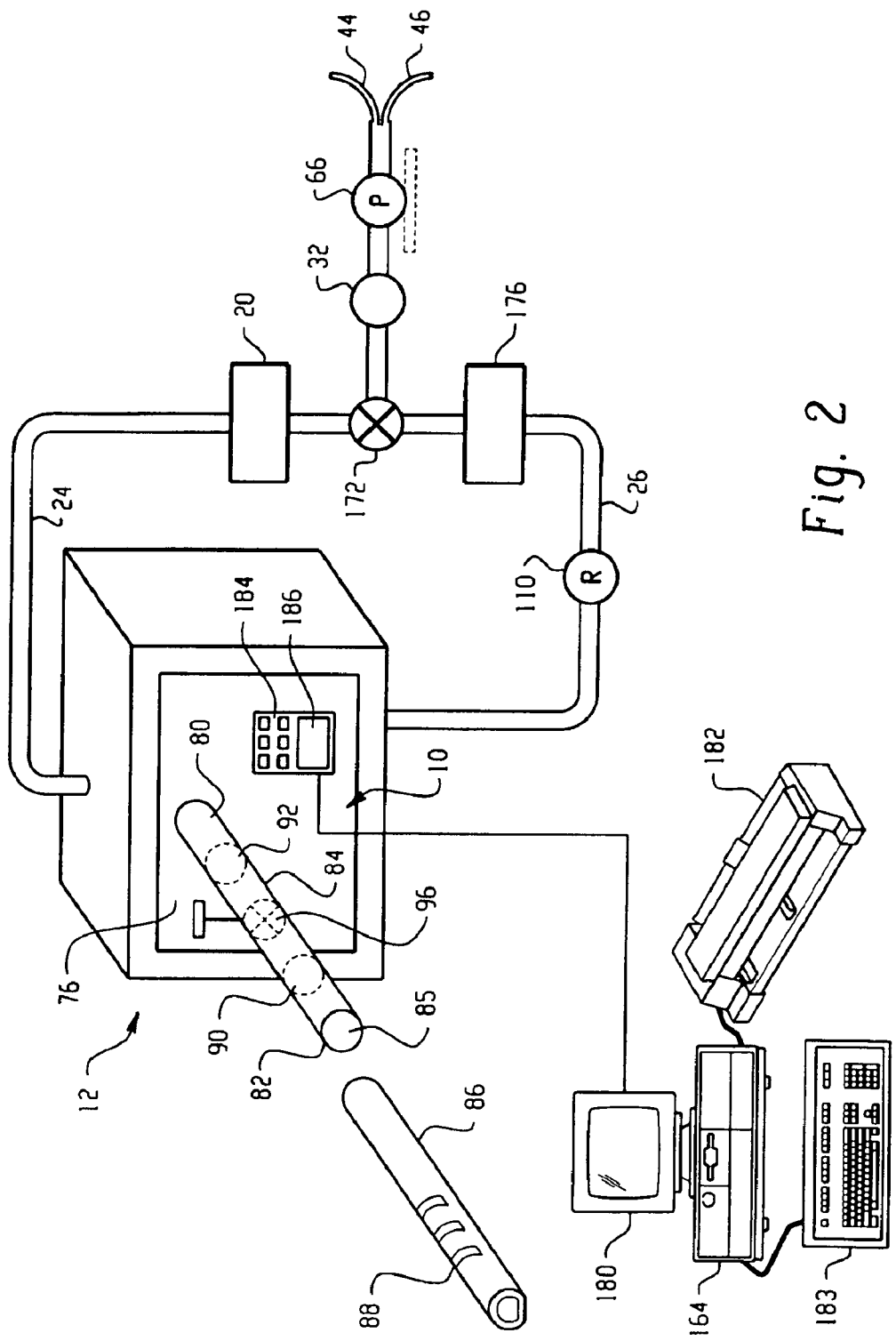
FIG. 2 is a schematic drawing showing a preferred door and tube in accordance with the present invention.

With reference to FIGS. 1 and 2, a biological indicator evaluator resistometer (BIER) vessel is shown. The BIER vessel is suited to the evaluation of the effects of vapor and gaseous sterilants on biological indicators, for D-value determination of biological indicators, and study of chemical indicators, chemical kinetics, material compatibility, process development, sensor or instrument calibration, packaging, and other material device evaluations.

Biological indicators typically contain a known population of a selected microorganism, such as a bacterial spore, which is known to be at least as resistant to a vapor sterilization process as the microorganisms that the sterilization process is expected to kill or deactivate. After the sterilization process, the microorganism is cultured in a growth medium for a sufficient period for any remaining viable microorganisms to grow. The growing microorganisms are detected by physical examination or by other known techniques. Chemical indicators contain a chemical (or chemicals) which exhibits a detectable change, such as a chemical or physical change, on exposure to the sterilization process. For example, the chemical may react with the sterilant to produce a color change.

The vessel includes a chamber wall 10 which defines an interior chamber 12. A vapor entry port 14 and a vapor exit port 16 are defined in the chamber wall 10. A generator 20 supplies the chamber 12 with a sterilant vapor, preferably a vaporized peroxy compound, such as hydrogen peroxide, peracetic acid vapor, or a mixture thereof, entrained in a carrier gas, such as air.

While the system will be described with particular reference to vapor hydrogen peroxide as the sterilant, it will be appreciated that other vaporous and gaseous sterilants are contemplated. Moreover, while reference is made to sterilants and sterilization, it will be appreciated that the system is also useful for assessing other levels of microbial decontamination, including disinfection and sanitization.

A circulating system includes a vapor inlet line 24, which carries the vapor from the generator 20 to the entry port 14. The hydrogen peroxide passes through the chamber 12 and leaves the chamber through the exit port 16. Optionally, a return line 26 returns the hydrogen peroxide to the generator. Alternatively, the vapor leaving the chamber 12 is directed through a destroyer, such as a catalytic converter 32 which converts the vapor to non-harmful products, such as water and oxygen. Vaporized hydrogen peroxide is flowed through the chamber 12 until selected sterilization conditions are reached in terms of temperature, pressure and hydrogen peroxide concentration.

The generator 20 is preferably one which generates a controllable stream of vaporized hydrogen peroxide. A particularly preferred generator is one which vaporizes droplets of liquid hydrogen peroxide on a heated plate and entrains the vapor in a stream of carrier gas, such as air. The gas is then transported with the vapor to the chamber 12.

The liquid hydrogen peroxide is optionally supplied from a single source 34 as a mixture of hydrogen peroxide in water for example, a 5–95% by weight hydrogen peroxide solution, more preferably, 30–35% hydrogen peroxide. The liquid components are entirely converted to vapor, so the resulting vapor has the same concentration of hydrogen peroxide as the liquid from which it is generated.

Figure 3:
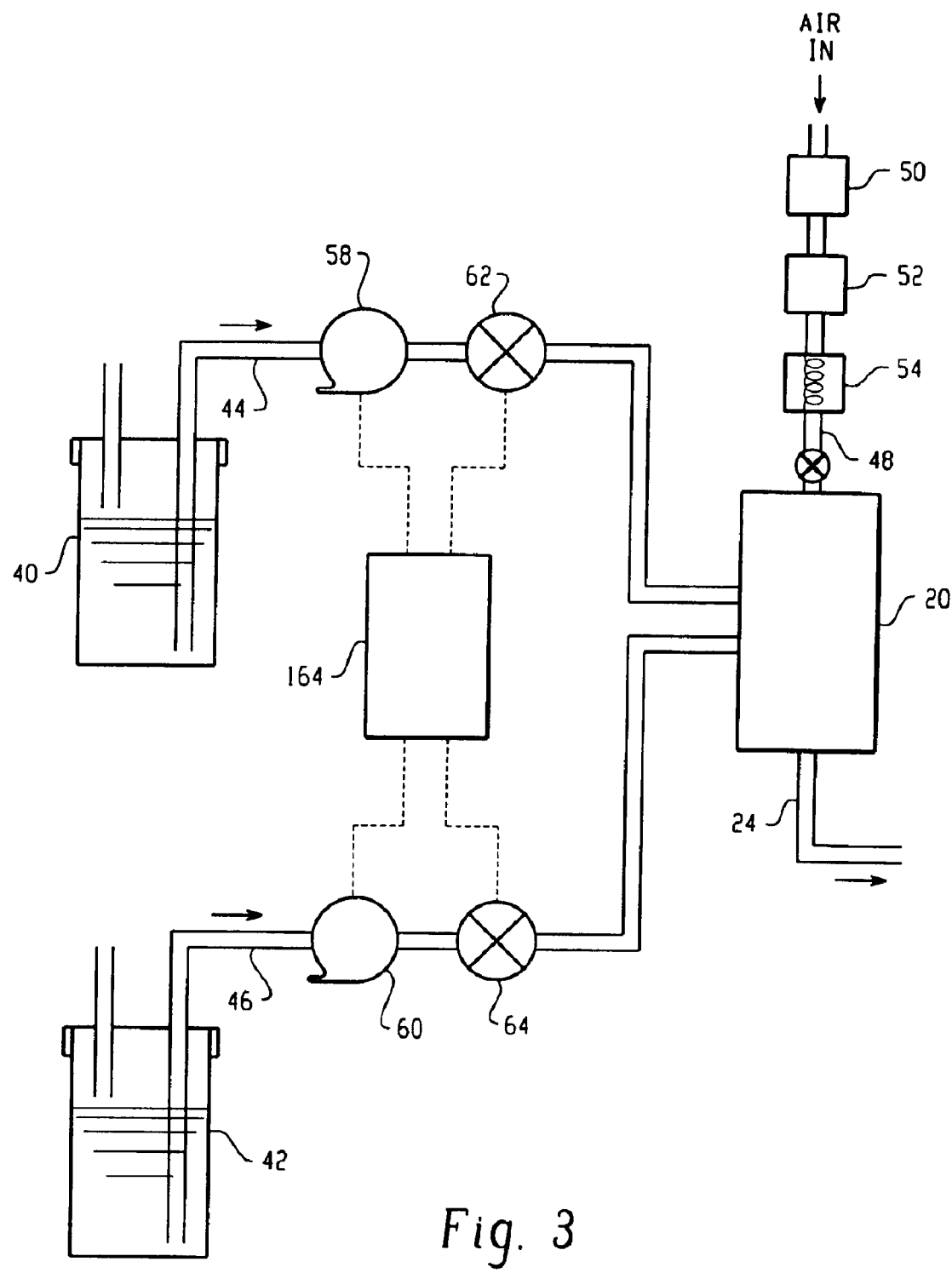
FIG. 3 is a schematic view of one embodiment of the sterilant supply system of FIG. 1.

With reference to FIG. 3, in an alternative embodiment, the components of the vapor are separately contained so that the composition of the vapor is adjustable by varying the rate of supply of each component to the vaporizer 20. A source, such as a reservoir 40 of concentrated hydrogen peroxide and a source 42 of water (or more dilute hydrogen peroxide), which may be a reservoir, as shown in FIG. 3, or a water supply line, are connected with the vaporizer 20 by supply lines 44 and 46, respectively. The two sources 40, 42 are separate so that the hydrogen peroxide solution and water can be supplied to the generator at separately variable rates. For example, the concentration of hydrogen peroxide in the multi-component vapor is adjustable by increasing the rate at which the concentrated hydrogen peroxide solution is supplied to the vaporizer, or by lowering the rate at which the water (or dilute hydrogen peroxide solution) is supplied, or by both increasing rate at which the concentrated hydrogen peroxide solution is supplied and lowering the rate at which the water/dilute solution is supplied. In this way, there is the opportunity to increase the concentration of hydrogen peroxide in the chamber 12 without simultaneously increasing the water vapor concentration.

It will be appreciated that the hydrogen peroxide in the reservoir 40 typically contains water, but the water concentration of the hydrogen peroxide solution is preferably at or below the minimum desired concentration of water in the chamber 12, so that different selected hydrogen peroxide concentrations are achieved by mixing fluid from both reservoirs 40, 42 in selected ratios. Additionally, since hydrogen peroxide decomposes in the chamber, generating water vapor, the ratio of the two components in the feed is preferably varied, as appropriate, throughout a single sterilization test to maintain the hydrogen peroxide concentration and water vapor (humidity) levels in the chamber independently at desired levels. Thus, the hydrogen peroxide concentration of the liquid entering the vaporizer towards the end of a sterilization test is preferably slightly higher than the selected hydrogen peroxide concentration in the chamber.

When a two source system is used, as shown in FIG. 3, removing the spent vapor from the chamber may not be necessary, other than to accommodate pressure changes due to the additional vapor entering through the inlet (or may take place at a lower rate than in a single source system). This is because the relative concentration of the vapor can be adjusted or maintained at a selected level primarily by adjusting the ratio of the two components in the feed. Thus, the overall consumption of hydrogen peroxide liquid is generally lower when separate sources 40, 42 of hydrogen peroxide and water are employed.

In contrast, if a single source 34 of hydrogen peroxide/water is used, as shown in FIG. 1, the water vapor concentration tends to increase with time, due to the conversion of hydrogen peroxide to water. To compensate for this, it is preferable to remove the spent vapor from the chamber at a relatively rapid rate and replenish it with fresh vapor at the desired hydrogen peroxide concentration.

The vaporized mixture of water and hydrogen peroxide is mixed with a carrier gas, such as air, which is supplied to the vaporizer through a line 48 (FIG. 3). A filter 50, such as a HEPA filter, preferably filters the air. The air may also be passed through a drier 52, to remove moisture, and through a heater 54, to raise the temperature of the carrier gas, prior to mixing the carrier gas with the hydrogen peroxide vapor.

In the embodiment of FIG. 3, first and second pumps 58, 60 pump the hydrogen peroxide solution and water from the reservoirs 40 and 42, respectively. In the embodiment of FIG. 1, a single pump (not shown) pumps the solution from the reservoir 34 to the generator 20. Separately adjustable regulator valves 62, 64 regulate the fluid flow rate through the lines 44, 46. Alternatively, regulation of the flow rates is adjusted by adjusting the pumping rate of the pumps 58, 60. In an alternative embodiment, shown in FIG. 2, a single pump 66 replaces pumps 58, 60.

The chamber wall 10 is preferably constructed from a material which exhibits low reactivity towards hydrogen peroxide, such as passivated stainless steel. Preferably, the chamber wall 10 is of rigid construction to allow for exposures requiring sub-atmospheric pressures or elevated pressures, and for maintaining the internal pressure. Fluctuations in pressure are not uncommon in conventional BIER vessels due to changes in ambient conditions and the flexibility of the chamber walls. Decreasing the flexibility in the walls 10 improves the reproducibility of the test conditions. A particularly preferred chamber 12 is one with a volume of about 0.7 cubic meters or less. Significantly smaller volumes are not required where the gaseous hydrogen peroxide generator 20 is one which can control the concentration and flow accurately.

With reference once more to FIG. 1, a thermal jacket 68, such as a water jacket or a resistance heater, surrounds substantially all of the chamber 12. The jacket 68 serves to maintain a selected temperature within the chamber. A heater 70, connected to the thermal jacket 68, heats the jacket. Alternatively, or additionally, the chamber 12 is insulated to reduce heat loss from the chamber. Where sub-ambient exposure temperatures are required, the thermal jacket 68 optionally includes a cooling device, such as a cold water jacket. In a particularly preferred embodiment, additional insulation of unjacketed areas, such as doors, further serves to maintain the internal temperature of the chamber 12.

With continued reference to FIG. 1, an opening 74 in the chamber wall 10 is sealed by a door 76. Optionally the door is heated to assist in maintaining a uniform temperature within the chamber. The door 76 opens to allow access to the chamber for repairs and maintenance, and optionally to introduce biological indicators and larger items through the opening 74 into the chamber 12. More preferably, the biological indicators are introduced to the chamber through a small opening 80 formed in the door 76, or elsewhere in the chamber wall 10. As shown in FIGS. 1 and 2, an access port 82 permits rapid insertion of items to be tested into the chamber without unduly perturbing the chamber conditions. The access port preferably includes a hollow tube 84, which extends outwardly from the door 76 around the opening 80. The tube 84 defines an interior passageway 85, which is shaped to receive a sample holder or D-tube 86. As shown in FIG. 2, both the tube 84 and the sample holder 86 have D-shaped cross sections to ensure proper orientation of the sample holder when inserted through the tube into the chamber, although other configurations are also contemplated.

Figure 4:
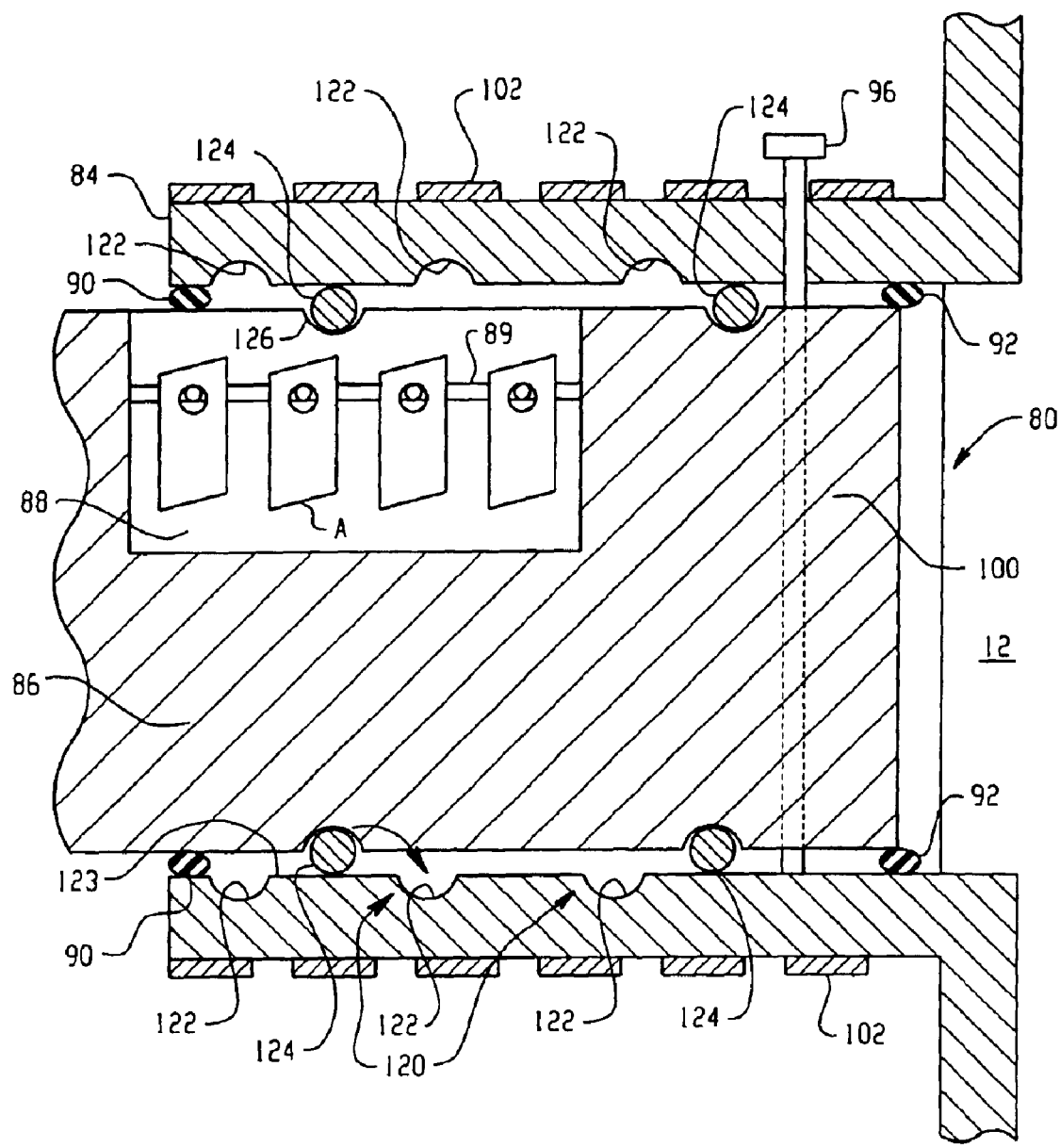
FIG. 4 is a side sectional view of one embodiment of the sample holder and access port of FIG. 1.

The sample holder 86 has a number of slots 88 or other receptacles for holding items A, such as biological indicators, to be exposed to the chamber conditions. Or, as shown in FIG. 4, items may be supported on a rod 89 in a single slot 88.

Preferably, the access port 82 is constructed to minimize the flow of gas or vapor into or out from the chamber 12 while the biological indicators are being admitted to the chamber to avoid perturbing the equilibrium conditions. The biological indicators are thus exposed relatively instantaneously to the preselected equilibrium sterilization conditions. In this respect, two seals 90, 92 are mounted within the tube 84 (FIG. 1). The seals 90, 92 may be in the shape of generally annular rings, formed, for example, from rubber, which form a seal between the sample holder 86 and the tube 84. Or, the seals may be in the shape of flap valves, or the like. Alternatively, the seals may be mounted on the sample holder 84, for example, in annular grooves on the exterior.

When not in use, the tube interior passageway 85 is closed by a valve 96. As shown in FIG. 1, the sample holder 86 is long enough that a rearward end 98 of the sample holder remains in the port 82 when a forward end 100 of the holder is fully inserted into the chamber 12. In this position, at least one of the seals 90, 92 contacts the exterior surface of the rearward end of the holder and thereby inhibits leakage of fluid into or out of the chamber 12. Prior to insertion, the seal(s) contact the forward end 100 of the sample holder and inhibit leakage. As can be seen from FIG. 1, both the forward and rear ends 98, 100 are closed, the slot or slots 88 forming an intermediate portion of the sample holder 86 between the two ends.

To insert the sample holder 86 into the chamber, the operator pushes the sample holder into the tube until the forward end 100 reaches the valve 96. At this time, the exterior seal 90 is in engagement with the forward end 100 of the sample holder. Preferably, a heating element 102, such as a heating tape, or other suitable heating element, surrounds the tube 86, at least in the region where the samples are placed (See FIG. 4). The sample holder 86 may be left in this position for a sufficient time to allow the indicators A, or other samples in the sample holder, to warm up, preferably to reach the chamber temperature. This inhibits or prevents condensation on the samples which could otherwise occur if cold samples are inserted into the chamber 12.

The operator then opens the valve 96 and quickly pushes the sample holder 86 as far as it will go into the chamber. This movement correctly and reproducibly positions the biological indicators in the chamber. The space between the sample holder and the tube 84 is closed by at least one of the seals 90, 92 at all times during insertion and exposure. As shown in FIG. 1, a stop in the form of a projection 103 optionally extends from the wall 10 to position the forward end 100 away from the wall. Alternatively, or additionally the stop may be in the form of a flange 103' which extends radially from the rearward end 98 of the sample holder. The flange 103 engages the tube 84 and limits the inward movement of the sample holder.

After a selected exposure period, the indicators are removed from the chamber 12, by reversing the insertion process, and evaluated for remaining biological activity, or otherwise examined to determine the effects of the sterilization process or other factors related to the indicators or process under investigation.

In the illustrated embodiment, a fan, or fans 104, preferably disposed within the chamber 12, mixes the gases within the chamber, thereby improving the uniformity of the mixture and increasing the rate of flow of sterilant over the biological indicators. Perforated upper and lower plates 106 and 108, respectively, disposed within the chamber, serve to induce a laminar flow of gas through the chamber, thereby more closely resembling the flow of vaporized hydrogen peroxide through certain conventional sterilization chambers. The fans 104 and plates 106 and 108 are positioned so that the vaporized hydrogen peroxide entering the chamber 12 is first mixed by the fans and then passes through the first plate 106 before flowing over the biological indicators A. The vaporized hydrogen peroxide then passes over the lower plate 108 before leaving the chamber 10. Without the perforated plates 106 and 108, turbulent flow sterilizers are simulated.

Optionally, the flow of vaporized hydrogen peroxide from the generator 20 is further controlled by a flow control device 110, such as a pump, vacuum source or blower, damper, or other regulator, which serves to regulate the flow of vaporized hydrogen peroxide into or out from the chamber 12. Preferably, the flow control device 110 is located in the inlet line 24 or the return line 26.

With particular reference to FIG. 4, an embodiment of the tube 84 and sample holder 86 suited to use in a vacuum chamber 12 is shown. When the chamber 12 is subjected to a vacuum, the suction on the sample holder 86 tends to draw the sample holder back along the tube 84 and into the chamber after the sample holder has been withdrawn. To ensure that the exposed sample holder is not accidentally drawn back into the chamber 12 by the vacuum, a tube engagement system 120 is provided. The system 120 preferably includes one or more indents, such as annular grooves 122 (three are shown in FIG. 4), formed in either an interior surface 123 of the tube wall or on the sample holder 86. The indents 122 receive biased elements 124, such as spring-biased ball bearings, carried by the other of the interior surface of the tube wall 123 or on the sample holder 86. As shown in FIG. 4, the ball bearings 124 are retained in sockets 126, and are carried by the sockets as the sample holder moves in or out of the chamber 12. When the sample holder 86 is drawn back toward the chamber 12 by vacuum pressure, the ball bearings 124 are biased outwardly from their sockets 126 and on reaching an adjacent groove 122, enter the groove. The sample holder 86 is thereby locked to the tube 84 inhibiting further movement of the sample holder 86 along the tube 84. The griping force provided by the engagement of the ball bearings in the groove may be overcome, if needed, by pulling on the sample holder with the hand.

With reference once more to FIG. 1, probes 160, such as temperature, pressure and humidity probes, are disposed within the chamber 12. The probes 160 serve to measure the chamber environment. The probes are connected to a monitor 162 which monitors the changes in environmental conditions. Preferably, the monitor 162 signals a controller 164 which controls the environmental conditions within the chamber 12 by controlling the heater 70 for regulating the temperature of the thermal jacket 68 and also the operation of the flow control 110, the vaporized hydrogen peroxide generator 20, the pumps 58, 60, and the valves 62, 64.

A sensor 166 is also positioned within the chamber to detect hydrogen peroxide concentration directly and/or detect the concentration of other components of the vapor from which the hydrogen peroxide concentration can be established indirectly. The sensor is preferably a radiation sensor, such as an infrared sensor. In one embodiment, the sensor uses near infrared (NIR) detection at two specific wavelengths, one corresponding to a predominantly hydrogen peroxide peak, the other to a water peak. There is some overlap between the peroxide and water peaks. By manipulating the data, the contribution of water is subtracted out and the hydrogen peroxide concentration determined.

Optionally, a vacuum source 170, such as a pump, evacuates the chamber 12 before, during, or after the sterilization process. Optionally, a three-way valve 172 in line 26 is connected to the vacuum pump 170. By switching the valve 172 between a first position, in which chamber gases passing through line 26 are returned to the generator 20, to a second position in which the chamber gases are directed to the pump 170, the chamber 12 is evacuated. Optionally, a catalytic converter 174 and drier 176 decompose the peroxy vapor and dry and heat the air before it is reintroduced into the generator 10.

More preferably, the system is used without recirculation of hydrogen peroxide or carrier gas. The air and hydrogen peroxide flows through the chamber in a single pass then is vented from the chamber via the catalytic converter 32. This provides for better control of the system.

With reference to FIG. 2, the controller 164 may take the form of a personal computer with a monitor 180 which displays the set parameters and other relevant information, such as the actual values of the parameters on a screen. The computer may be hooked up to a printer 182, which provides a printout of the cycle conditions at the end of a cycle. The operator interfaces with the controller via a user interface, such as a keyboard 183, keypad 184, touch screen 186, or the like. In a preferred embodiment, the controller feeds prompts to a display on the touch screen 186 and the operator enters the desired cycle parameters on the touch screen in response to the prompts. The controller 164 then controls the cycle in accordance with the selected parameters. The controller optionally signals an alarm and/or aborts the cycle in the event that the parameters cannot be achieved, or example, if there is a leak in the system or one of the reservoirs 40, 42 becomes empty.

As will be appreciated, the controller 164 and user interface 183, 184, 186 may be integrally packaged with the chamber 12 and have dedicated software for ease of operator use. The touch screen may be mounted, for example, to the door 76 or wall 10 of the chamber for ease of access.

If the hydrogen peroxide concentration is lower than a target level, the controller 164 has a number of options, including increasing the hydrogen peroxide concentration in the chamber by increasing the vaporization rate or by increasing the proportion of hydrogen peroxide in the liquid flowing to the vaporizer by adjusting the valve 62 and/or valve 64. Having two separate reservoirs, one for hydrogen peroxide and one for water, allows for more careful control of chamber conditions. The hydrogen peroxide concentration of the chamber can thus be adjusted up or down independently of the water vapor concentration (humidity). For example, if the controller 164 adds hydrogen peroxide to the chamber, this will displace some of the air and water in the chamber (i.e., by reducing the concentration of the water), and also increase the pressure within the chamber. The controller automatically compensates for these changes by allowing gas to leave the chamber to maintain the desired set point pressure and by adding additional water to maintain the set point water concentration. By using suitably tuned control algorithms, the controller rapidly stabilizes the chamber parameters, such as temperature, pressure, humidity, and hydrogen peroxide concentration, at the set points and maintains the steady state during an exposure cycle.

The chamber 12 is preferably brought to the desired exposure conditions prior to insertion of the biological indicators or other items to be exposed. Thus, the indicators equilibrate rapidly to the exposure conditions. Similarly, on withdrawal of the indicators from the chamber, the process of withdrawal quickly stops the sterilization process by rapidly removing the indicators from the sterilizer.

The invention has been described with reference to the preferred embodiment. Obviously, modifications and alterations will occur to others upon reading and understanding the preceding detailed description. It is intended that the invention be construed as including all such modifications and alterations insofar as they come within the scope of the appended claims or the equivalents thereof.

Having thus described the preferred embodiment, the invention is now claimed to be:

1. A system for evaluating biological indicators comprising:
   a) a chamber;
   b) an access port for selectively introducing biological indicators into the chamber and for subsequently removing the biological indicators from the chamber;
   c) a generator for generating a multi-component sterilant vapor;
   d) a circulating system for supplying the multi-component sterilant vapor to the chamber;
   e) a source of a first component of the multi-component sterilant vapor fluidly connected with the vaporizer; and
   f) a source of a second component of the multi-component sterilant vapor, separate from the first source, fluidly connected with the vaporizer.

2. The system of claim 1, wherein the multi-component sterilant vapor comprises a vaporized peroxy compound and water vapor.

3. The system of claim 2, wherein the peroxy compound includes at least one of hydrogen peroxide and peracetic acid.

4. The system of claim 1, further including:
   at least one regulator which regulates the flow of one of the first and second components to the generator.

5. The system of claim 1, wherein the chamber is constructed of a material that is rigid under vacuum and pressure and further including a pump for at least one of drawing the chamber to sub-atmospheric pressure and pumping the chamber to above-atmospheric pressure.

6. The system of claim 1, further including a heater for selectively heating or a cooling system for cooling walls of the chamber.

7. The system of claim 1, further including a fan for mixing gases within the chamber.

8. The system of claim 1, further including a sample holder for supporting items within the chamber.

9. The system of claim 8, wherein the access port includes a tube configured for receiving the sample holder.

10. The system of claim 9, wherein the access port further includes a valve for selectively closing the tube to seal the chamber.

11. The system of claim 9, wherein the access port includes at least one seal, the seal engaging a first portion of the sample holder when a second portion of the sample holder is positioned within the chamber.

12. The system of claim 1, wherein the circulating system circulates the multi-component sterilant vapor through the chamber and includes a device for controlling a flow rate of the multi-component sterilant vapor through the chamber.

13. The system of claim 1, further including probes for measuring environmental conditions within the chamber.

14. The system of claim 1, further including a controller for monitoring environmental conditions within the chamber, the controller controlling at least one of:
- a heater for heating the chamber,
- a cooling system for cooling the chamber,
- a fan for circulating the multi-component sterilant vapor through the chamber,
- a pump for adjusting pressure within the chamber,
- a regulator for regulating component flow into the chamber, and
- the generator.

15. A system for evaluating biological indicators comprising:
   a) a chamber;
   b) an access port for selectively introducing biological indicators into the chamber and for subsequently removing the biological indicators from the chamber, the access port including:
      a tube having a cross section shaped to receive a sample holder therethrough and an opening in fluid communication with the chamber at one end thereof, and
      a valve which selectively closes the opening;
   c) a generator for generating a multi-component sterilant vapor;
   d) a circulating system for supplying the multi-component sterilant vapor to the chamber.

16. The system of claim 15, further including:
   at least one seal mounted within the tube which contacts the sample holder to seal the access port during an exposure cycle.

17. A method of evaluating a biological indicator comprising:
   generating a multi-component vapor from a first component and a second component;
   passing the multi-component vapor through a test chamber until steady state conditions are achieved;
   introducing the biological indicator to be evaluated into the chamber;
   maintaining the steady state conditions for a selected period, including adjusting a ratio of the first component to the second component in the multi-component vapor and introducing the adjusted multi-component vapor to the test chamber;
   removing the biological indicator from the test chamber after a preselected time period;
   assessing the effects upon the indicator.

18. The method of claim 17, wherein the multi-component vapor includes at least one of hydrogen peroxide and peracetic acid vapor.

19. The method of claim 17, further including monitoring and controlling temperature within the chamber.

20. The method of claim 17, further including monitoring and controlling the pressure within the chamber.

21. The method of claim 17, further including monitoring environmental conditions in the test chamber and controlling at least one of:
   flow of the multi-component vapor;
   temperature in the chamber;
   pressure in the test chamber.

22. The method of claim 17, further including positioning the biological indicator in a sample holder, the step of introducing the indicator including:
   inserting the sample holder through an access port, and, during the step of maintaining the steady state conditions:
   sealing a gap between an exterior portion of the sample holder and the access port.

23. An evaluation system:
   a vessel which defines an interior chamber;
   a source of an antimicrobial fluid which supplies the antimicrobial fluid to the chamber;
   a tube, fluidly connected with the chamber, which extends from the vessel for receiving a sample holder therein, the sample holder carrying a sample to be evaluated and being movable within the tube between a first position, in which the sample is positioned outside the chamber and a second position, in which the sample is positioned inside the chamber to be exposed to the antimicrobial fluid;
   means for applying suction to the chamber;
   means associated with at least one of the tube and the sample holder, for resisting movement of the sample holder into the chamber under the influence of a reduced pressure applied by the suction means.

24. The evaluation system of claim 23, wherein the resisting means include:
   a groove in one of the tube and the sample holder; and
   a biased element associated with the other of the tube and the sample holder, the biased element entering the groove as the sample holder is drawn into the chamber by the reduced pressure, resisting further movement of the sample holder into the chamber.

25. The evaluation system of claim 23, wherein the biased element includes a plurality of spring biased ball bearings.

26. The evaluation system of claim 23, wherein the groove includes a plurality of spaced, generally annular grooves.

27. The evaluation system of claim 23, further including a valve which selectively seals the chamber from the tube.

28. A method of evaluating an effect of an antimicrobial process upon an indicator for the process, the method including:
   a) supplying an antimicrobial fluid to the chamber;
   b) positioning the indicator on a sample holder;
   c) inserting the sample holder into a first end of a tube which is fluidly connected with a chamber at a second end;
   d) opening a valve which seals the chamber from the second end of the tube;
   e) pushing the sample holder through the tube until the indicator is positioned within the chamber;
   f) exposing the indicator to the antimicrobial fluid in the chamber;
   g) withdrawing the sample holder from the chamber; and
   h) evaluating the indicator to determine the effect of the antimicrobial process upon the indicator.

* * * * *